United States Patent [19]

Franzmair

[11] Patent Number: 4,603,196
[45] Date of Patent: Jul. 29, 1986

[54] PROCESS FOR THE PREPARATION OF β-METHYLDIGOXIN

[75] Inventor: Rudolf Franzmair, Linz, Austria

[73] Assignee: Chemie Linz Aktiengesellschaft, Linz, Austria

[21] Appl. No.: 612,561

[22] Filed: May 21, 1984

Related U.S. Application Data

[63] Continuation-in-part of Ser. No. 489,083, Apr. 27, 1983, abandoned.

[51] Int. Cl.$^4$ ............................................. C07J 17/00
[52] U.S. Cl. ........................................ 536/6.1; 536/5; 536/120
[58] Field of Search .................... 536/4.1, 6, 6.1, 5, 536/120

[56] References Cited

U.S. PATENT DOCUMENTS 4,145,528 3/1979 Pelan et al. ...................... 536/6.1

FOREIGN PATENT DOCUMENTS 1168970 10/1969 United Kingdom .
1274779 5/1972 United Kingdom .
1378605 12/1974 United Kingdom .
1545647 5/1979 United Kingdom .

Primary Examiner—Johnnie R. Brown
Assistant Examiner—Elli Peselev
Attorney, Agent, or Firm—Wenderoth, Lind & Ponack

[57] ABSTRACT

The invention relates to a process for the preparation of β-methyldigoxin by the selective methylation of digoxin with dimethyl sulfate in the presence of a basic strontium compound and, if appropriate, of an inert inorganic adsorbent. Strontium hydroxide octahydrate, strontium methylate or strontium hydroxymethylate is used as the basic strontium compound, and an oxide, silicate or phosphate of magnesium, calcium, aluminum, silicon or titanium, with a water content in the range of 0 to 20% by weight, is used as the inorganic adsorbent. The reaction is carried out at temperatures of −15° to 15° C. in the presence of 3 to 24 moles of water per mole of digoxin, the water being introduced in the reaction mixture by the water content of strontium hydroxide octahydrate and/or the inorganic adsorbent used and purification of the methylation product so formed by column chromatography on $SiO_2$ with a mixture of chlorohydrocarbon and a lower aliphatic alcohol.

9 Claims, No Drawings

PROCESS FOR THE PREPARATION OF β-METHYLDIGOXIN

This application is a continuation-in-part of Ser. No. 489,083, Apr. 27, 1983, abandoned May 21, 1984.

The invention relates to a process for the preparation of 4'''-O-methyldigoxin (β-methyldigoxin) by the partial methylation of digoxin.

The preparation of digoxin monoalkyl ethers by the monoalkylation of digoxin is known from the patent literature. In the process of British patent specification 1,168.970 the partial monomethylation of the 3'''- or 4'''-hydroxy group on the terminal digitoxose can be carried out with the customary methylating agents, such as diazomethane or dimentyl sulfate, under the process conditions which are in themselves known. However, in the methylation with dimethyl sulfate, diagoxin polyethers are formed in amounts of 20 to 30% by weight as by-products, and these can no longer be demethylated to give digoxin or monomethyldigoxin. These by-products must be separated off chromatographically and represent a considerable loss of expensive starting material.

The use of the poisonous and explosive diazomethane for the monomethylation of digoxin is not suitable for a large-scale manufacturing process.

In an improved process, such as that described in British patent specification No. 1,274.779, the use of diazomethane can be avoided and the selectivity of the monoalkylation reaction can be promoted if the reaction of digoxin with dimethyl sulfate, which is in itself known, is carried out in the presence of barium hydroxide and of a basic aluminum compound. In this process, a 45% yield of β-methyldigoxin can be achieved if the reaction is carried out in a mixture of dimethylformamide and toluene at room temperature and if aluminum oxide is added to the reaction mixture. To purify the crude β-methyldigoxin, which, in addition to unreacted digoxin, contains α-methyldigoxin and dimethyldigoxin as impurities, the reaction mixture is concentrated in vacuo, with the addition of pyridine, and the residue is freed of unreacted digoxin by the method of multiplicative partitioning between two solvent phases. The digoxin present in the aqueous phase is extracted with chloroform and conveyed to another methylation process.

It is known from British patent specification No. 1,378.605 to prepare β-methyldigoxin, as a starting material for the synthesis of 20,22-dihydro-4'''-O-methyl-digoxin, by reacting digoxin with dimethyl sulfate in the presence of strontium hydroxide and aluminum oxide at room temperature, and purifying the crude product by multiplicative partitioning, chloroform extraction and recrystallization from acetone. In the only example in the said Offenlegungsschrift which relates to the preparation of β-methyldigoxin, the reaction is carried out with a molar ratio of dimethyl sulfate to digoxin of 19:1. This process has the disadvantage that, for the methylation, a large excess of dimethyl sulfate is required, which must be removed again during the working-up of the crude product.

Finally, British patent specification No. 1,545.647 also describes the preparation of β-methyldigoxin by reacting digoxin with methyl esters of organic or inorganic sulfur acids in an inert atmosphere, and the purification of the methylation product by column chromatography on $SiO_2$.

In the last-mentioned process, the reaction is carried out using dimethyl sulfate as the methylating agent, in a mixture of dry dimethylformamide and dioxane, in the presence of strontium hydroxide and aluminum oxide at room temperature.

It has now been found that, surprisingly, in the monomethylation of digoxin in the 16-position of the terminal digitoxose, better results are achieved, in respect of selectivity and yield of the reaction, than indicated in the patent literature if the reaction is carried out at temperatures below room temperature in the presence of a basis strontium compound and, if appropriate, of an inert inorganic adsorbent, and if water is added to the organic reaction medium.

The present invention therefore relates to a process for the preparation of β-methyldigoxin by a selective monomethylation of digoxin which comprises methylating digoxin with dimethyl sulfate in a dimethylformamide/toluene mixture as solvent, in the presence of 1 to 3 moles of a basic strontium compound selected from the group consisting of strontium hydroxide octahydrate, strontium methylate and strontium hydroxymethylate and of 0 to 3 moles of a inert inorganic adsorbent selected from the group consisting of oxides, silicates and phosphates of magnesium, calcium, aluminium, silicon and titanium with a water content in the range of 0 to 20% by weight, said methylation being carried out at tempertures of $-15°$ C. to $15°$ C. in the presence of 3 to 24 moles of water per mole of digoxin, the water being introduced in the reaction mixture by the water content of strontium hydroxide octahydrate and/or the inorganic adsorbent used and purification of the methylation product so formed by column chromatography on $SiO_2$ with a mixture of chlorohydrocarbon and a lower aliphatic alcohol.

In a preferred embodiment of the present invention the basic strontium compound used is strontium hydroxide octahydrate and the methylation is carried out in the presence of 8 to 24 moles of water per mole of digoxin at a temperature of $-10°$ C. to $10°$ C., preferably of $-5°$ to $5°$ C.

In general, the process according to the invention is carried out by initially taking a solution of pure digoxin in a dimethylformamide/toluene mixture and treating this with the basic strontium compound and, if appropriate, the inert inorganic adsorbent. After thorough mixing and adjustment of the desired reaction temperature, a solution of dimethyl sulfate in toluene is added dropwise.

If strontium hydroxide octahydrate is used to regulate the pH value and to promote the selective progress of the methylation, it is not necessary to add an inert water-containing inorganic adsorbent to the reaction mixture. If, on the other hand, the reaction is carried out using strontium methylate or strontium hydroxymethylate as the basic strontium compound, the amount of water necessary for the smooth progress of the reaction is introduced into the reaction medium by adding an inert inorganic adsorbent with a water content of up to 20% by weight.

Preferred inorganic adsorbents are the oxides of elements of the 2nd, 3rd and 4th main groups of Mendeleev's periodic table, with a water content of 10–20% by weight, aluminum oxide, silica gel, titanium dioxide, kaolin and talc being particularly preferred.

The molar ratio of digoxin to basic strontium compound to dimethyl sulfate is generally 1:1 to 3:1 to 5. Within these limits, it is preferred and more economical to use 2 moles of the basic strontium compound per mole of digoxin. If the process according to the invention is carried out in the presence of an inorganic adsorbent, it is recommended to use 1 to 3 moles of the adsorbent, preferably 3 moles, per mole of digoxin. The amount of dimethyl sulfate used per mole of digoxin is preferably 2-3 moles.

The methylation product, which is usually purified beforehand, is introduced onto silica gel for separation by column chromatography, eluted with a mixture of a halogenohydrocarbon and a lower aliphatic alcohol, preferably a 9:1 mixture of methylene chloride and methanol, and fractionated. The fractions containing pure β-methyldigoxin are combined and freed of eluant in vacuo. The β-methyldigoxin isolated in this way can then be recrystallized, for example from acetone.

The pure β-methyldigoxin prepared by the process according to the invention is identified by thin layer chromatography, melting point and IR spectra.

The invention is illustrated in greater detail by the examples which follow.

The yields and selectivities of the reaction given in the examples are determined according to the following equations:

$$\text{Yield (\%)} = \frac{\beta\text{-methyldigoxin formed in moles}}{\text{digoxin used in moles}} \times 100$$

$$\text{Selectivity (\%)} = \frac{\beta\text{-methyldigoxin formed in moles}}{\text{digoxin converted in moles}} \times 100$$

EXAMPLE 1

2.34 g (3 millimoles) of digoxin are dissolved in 30 ml of warm dimethylformamide, the solution is treated with 30 ml of toluene and, after the addition of 1.59 g (6 millimoles) of strontium hydroxide octahydrate and 1.13 g (9 millimoles) of silica gel with a water content of 10% by weight, the mixture is stirred for half an hour at 0° C.

A solution of 1.14 g (9 millimoles) of dimethyl sulfate in 15 ml of toluene is then added dropwise in the course of half an hour, and the reaction mixture is stirred for 20 hours at 0° C. The mixture is then diluted with 150 ml of chloroform, stirred vigorously with 3 ml of water and filtered through silica gel, the silica gel is washed with 75 ml of chloroform and the filtrate is evaporated in vacuo after the addition of 5 ml of pyridine. The dry residue is taken up in 150 ml of chloroform and the mixture is washed with 3 times 50 ml of water. The combined wash waters are extracted with 50 ml of chloroform, and the chloroform phases are dried over sodium sulfate and evaporated. The residue is adsorbed on a silica gel column and eluted with a 9:1 mixture of methylene chloride and methanol. Evaporation of the fractions collected gives 200 mg (8.24% of theory) of dimethyldigoxin, 200 mg (8.55% of theory) of digoxin and 1.849 g (77.53% of theory) of β-methyldigoxin, which gives 1.801 g of pure β-methyldigoxin after recrystallization from acetone. The yield is 75.5% and the selectivity of the reaction is 82.57%.

EXAMPLES 2, 3, 4 AND 5

In the examples which follow, the monomethylation of digoxin is carried out with the same batch size and following the same procedure as in Example 1, but at different reaction temperatures. The reaction temperatures, yields and selectivities of the reaction are given in Table I.

TABLE I

| Example | Reaction temperature | Yield | Selectivity |
|---|---|---|---|
| 2 | −5° C. | 73.08% | 83.68% |
| 3 | 5° C. | 74.34% | 80.30% |
| 4 | 10° C. | 71.28% | 75.35% |
| 5 | 15° C. | 63.65% | 84.48% |

EXAMPLE 6

2.34 g (3 millimoles) of digoxin are dissolved in 30 ml of warm dimethylformamide, the solution is treated with 30 ml of toluene and, after the addition of 2.39 g (9 millimoles) of strontium hydroxide octahydrate, the mixture is stirred for half an hour at −10° C.

A solution of 1.14 g (9 millimoles) of dimethyl sulfate in 15 ml of toluene is then added dropwise in the course of half an hour, and the reaction mixture is stirred for 20 hours at −10° C. Working-up is carried out as in Example 1.

Evaporation of the fractions collected gives 174 mg (7.4% of theory) of dimethyldigoxin, 267 mg (11.4% of theory) of digoxin and 1.836 g (78.29% of theory) of β-methyldigoxin, from which 1.69 g of pure β-methyldigoxin are obtained after recrystallization from acetone. The yield is 72.06% and the selectivity of the reaction is 79.98%.

EXAMPLE 7

1.59 g (6 millimoles) of strontium hydroxide octahydrate are added, the batch size and the reaction conditions otherwise being the same as indicated in Example 6.

After evaporation of the fractions collected and recrystallization from acetone, this gives 1.76 g of pure β-methyldigoxin, which corresponds to a yield of 73.79% of theory.

EXAMPLE 8

1.59 g (6 millimoles) of strontium hydroxide octahydrate are added and the reaction is carried out at 0° C., the ratios of amounts and the procedure otherwise being the same as in Example 6.

After evaporation of the fractions collected and recrystallization from acetone, this gives 1.82 g of pure β-methyldigoxin, which corresponds to a yield of 76.31% of theory.

EXAMPLE 9

A solution of 2.34 g (3 millimoles) of digoxin is treated with 797 mg (3 millimoles) of strontium hydroxide octahydrate and the mixture is methylated with 757 g (6 millimoles) of dimethyl sulfate at 0° C., the procedure being the same as in Example 6. Evaporation of the fractions collected gives 119 mg (4.90% of theory of dimethyldigoxin, 403 mg (17.16%) of digoxin and 1.732 g (72.62% of theory) of β-methyldigoxin, from which 1.59 g of pure β-methyldigoxin are obtained after recrystallization from acetone. The yield is 66.67% and the selectivity of the reaction is 80.48%.

EXAMPLE 10

2.34 g of digoxin are dissolved in 30 ml of warm dimethylformamide, the solution is treated with 30 ml of toluene and, after the addition of 1.59 g (6 millimoles of strontium hydroxide octahydrate and 0.92 g (9 millimoles) of aluminum oxide with a water content of 20% by weight, the mixture is stirred for half an hour at 0° C. A solution of 1.14 g (9 millimoles) of dimethyl sulfate in 15 ml of toluene is then added dropwise in the course of half an hour, and the reaction mixture is stirred for 20 hours at 0° C. Working-up is carried out as in Example 1.

Evaporation of the fractions collected and recrystallization from acetone gives 1.78 g of pure β-methyldigoxin, which corresponds to a yield of 74.63% of theory.

EXAMPLE 11

2.34 g (3 millimoles) of digoxin are dissolved in 30 ml of warm dimethylformamide, the solution is treated with 30 ml of toluene and, after the addition of 0.9 g (6 millimoles) of strontium methylate and 0.92 g (9 millimoles) of aluminum oxide with a water content of 20% by weight, the mixture is stirred for half an hour at 0° C. A solution of 1.14 g (9 millimoles) of dimethyl sulfate in toluene is then added dropwise in the course of half an hour, and the reaction mixture is stirred for 20 hours at 0° C. Working-up is carried out as in Example 1. Evaporation of the fractions collected gives 1.323 g (55.47% of theory) of β-methyldigoxin, which gives 1.20 g of pure β-methyldigoxin after recrystallization from acetone. The yield is 50.31% and the selectivity of the reaction is 50.94%.

EXAMPLE 12

814 mg (6 millimoles) of strontium hydroxymethylate are added as the basic strontium compound, the batch sizes and the procedure otherwise being the same as in Example 11.

After evaporation of the fractions collected, this gives 415 mg (17.71% of theory) of dimethyldigoxin, 120 mg (5.25% of theory) of digoxin and 1.686 g (70.69% of theory) of β-methyldigoxin, from which 1.59 g of pure β-methyldigoxin are obtained after recrystallization from acetone. The yield is 66.67% and the selectivity of the reaction is 70.36%.

EXAMPLE 13

2.34 g (3 millimoles) of digoxin are dissolved in 30 ml of warm dimethylformamide, the solution is treated with 30 ml of toluene and, after the addition of 1.59 g (6 millimoles) of strontium hydroxide octahydrate and 719 mg (9 millimoles) of titanium dioxide, the mixture is stirred for half an hour at 0° C.

A solution of 1.14 g (9 millimoles) of dimethyl sulfate in 15 ml of toluene is then added dropwise in the course of half an hour, and the reaction mixture is stirred for 20 hours at 0° C. Working-up is carried out as in Example 1.

Evaporation of the fractions collected gives 402 mg (16.6% of theory) of dimethyldigoxin, 72 mg (3.07% of theory) of digoxin and 1.727 g (72.41% of theory) of β-methyldigoxin, from which 1.585 g of pure β-methyldigoxin are obtained after recrystallization from acetone. The yeild is 66.46% and the selectivity of the reaction is 68.56%.

EXAMPLE 14

1.55 g (9 millimoles) of calcium hydrogenphosphate dihydrate are added as the inorganic adsorbent, the batch size and the reaction conditions otherwise being the same as in Example 13.

Evaporation of the fractions collected gives 367 mg (15.12% of theory) of dimethyldigoxin, 77 mg (3.29% of theory) of digoxin and 1.636 g (68.6% of theory) of β-methyldigoxin, from which 1.425 g of pure β-methyldigoxin are obtained from recrystallization from acetone. The yield is 59.75% and the selectivity of the reaction is 61.78%.

EXAMPLE 15

1.46 g (9 millimoles) of kaolin are added as the inorganic adsorbent, the batch size and the reaction conditions otherwise being the same as in Example 13.

Evaporation of the fractions collected gives 278 mg (11.44% of theory) of dimethyldigoxin, 105 mg (4.48% of theory) of digoxin and 1.733 g (72.66% of theory) of β-methyldigoxin, from which 1.62 g of pure β-methyldigoxin are obtained after recrystallization from acetone. The yield is 67.93% and the selectivity of the reaction is 71.11%.

EXAMPLE 16

1.5 g of talc are added as the inorganic adsorbent, the batch size and the reaction conditions otherwise being the same as in Example 13.

Evaporation of the fractions collected gives 356 mg (14.67% of theory) of dimethyldigoxin, 99 mg (4.23% of theory) of digoxin and 1.804 g (75.64% of theory) of β-methyldigoxin, from which 1.694 g of pure β-methyldigoxin are obtained after recrystallization from acetone. The yield is 71.03% and the selectivity of the reaction is 75.49%.

What I claim is:

1. A process for the preparation of β-methyldigoxin by a selective monomethylation of digoxin which comprises methylating digoxin with dimethyl sulfate in a mixture of dimethylformamide and toluene as solvent, in the presence of 1 to 3 moles of a basic strontium compound selected from the group consisting of strontium hydroxide octahydrate, strontium methylate and strontium hydroxymethylate, and 0 to 3 moles of an inert inorganic adsorbent selected from the group consisting of oxides, silicates and phosphates of magnesium, calcium, aluminium, silicon and titanium with a water content in the range of 0 to 20% by weight, said methylation being carried out at −15° C. to 15° C. in the presence of 3 to 24 moles of water per mole of digoxin, said water being introduced in the reaction mixture by the water content of at least one of the strontium hydroxide octahydrate and the inorganic adsorbent used, and purifying the methylation product so formed by column chromatography on $SiO_2$ with a mixture of a chlorohydrocarbon and a lower aliphatic alcohol.

2. The process as claimed in claim 1, wherein the basic strontium compound is strontium hydroxide octahydrate and the methylation is carried out in the presence of 8 to 24 moles of water per mole of digoxin.

3. The process as claimed in claim 1, wherein the methylation is carried out at temperatures of −5° C. to 5° C.

4. The process as claimed in claim 1, wherein 2 moles of the basic strontium compound are used per mole of digoxin.

5. The process as claimed in claim 1, wherein 3 moles of the insert inorganic adsorbent are used per mole of digoxin.

6. The process as claimed in claim 1, wherein the inorganic adsorbent is selected from the group consisting of the oxides of magnesium, calcium, aluminium and silicon with a water content of 10 to 20% by weight.

7. The process as claimed in claim 1, wherein the methylation of digoxin is carried out in the presence of strontium hydroxide octahydrate without the addition of the inert inorganic adsorbent.

8. The process as claimed in claim 1, wherein the methylation of digoxin is carried out in the presence of strontium methylate or strontium hydroxymethylate and 3 moles per mole of digoxin of the inert inorganic adsorbent with a water content of 20% by weight.

9. The process as claimed in claim 1, wherein 2-3 moles of the dimethyl sulfate are used per mole of digoxin.

* * * * *